(12) United States Patent
Pozzi et al.

(10) Patent No.: US 8,847,601 B2
(45) Date of Patent: Sep. 30, 2014

(54) METHOD OF DETERMINING THE MAXIMUM TEMPERATURE UNDERGONE BY A SEDIMENTARY ROCK, ESPECIALLY IN THE FIELD OF HYDROCARBON FORMATION

(76) Inventors: Jean Pierre Pozzi, Paris (FR); Charles Aubourg, Voiron (FR)

( * ) Notice: Subject to any disclaimer, the term of this patent is extended or adjusted under 35 U.S.C. 154(b) by 641 days.

(21) Appl. No.: 13/133,592

(22) PCT Filed: Dec. 4, 2009

(86) PCT No.: PCT/FR2009/001391
§ 371 (c)(1),
(2), (4) Date: Jun. 8, 2011

(87) PCT Pub. No.: WO2010/066961
PCT Pub. Date: Jun. 17, 2010

(65) Prior Publication Data
US 2011/0241688 A1    Oct. 6, 2011

(30) Foreign Application Priority Data
Dec. 10, 2008  (FR) ...................................... 08 06921

(51) Int. Cl.
*G01V 3/00*  (2006.01)
*G01N 33/24*  (2006.01)

(52) U.S. Cl.
CPC ..................................... *G01N 33/24* (2013.01)
USPC ........... 324/345; 324/331; 324/326; 324/340; 324/323; 324/441; 324/224

(58) Field of Classification Search
USPC .......... 324/331, 326, 340, 323, 345, 441, 224
See application file for complete search history.

(56) References Cited

U.S. PATENT DOCUMENTS

| | | | | |
|---|---|---|---|---|
| 4,701,712 A * | 10/1987 | Seeley et al. | .................. | 324/340 |
| 6,769,805 B2 * | 8/2004 | Williams et al. | .............. | 374/137 |
| 6,998,845 B2 * | 2/2006 | Martin et al. | .................. | 324/346 |
| 8,230,918 B2 * | 7/2012 | Ameen | ...................... | 166/250.1 |

* cited by examiner

*Primary Examiner* — Arleen M Vazquez
*Assistant Examiner* — Alesa Allgood
(74) *Attorney, Agent, or Firm* — Sughrue Mion, PLLC

(57) ABSTRACT

A method of determining the maximum temperature undergone by a specimen of sedimentary rock during natural heating over a geological process, within the range from 60° C. to 230° C. approximately. The method includes analysis at very low temperature, down to a few kelvin, for example down to 10 kelvin, of the magnetic transitions intended to characterize an iron oxide and an iron sulfide that are formed or destroyed in the specimen by the geological heating of the sediment; and determination of the maximum temperature undergone by the specimen, using a calibration obtained by measuring the same magnetic parameters on the same sediment or on other sediments of the same nature, heated beforehand in the laboratory to known temperatures.

12 Claims, 1 Drawing Sheet

Figure 1:
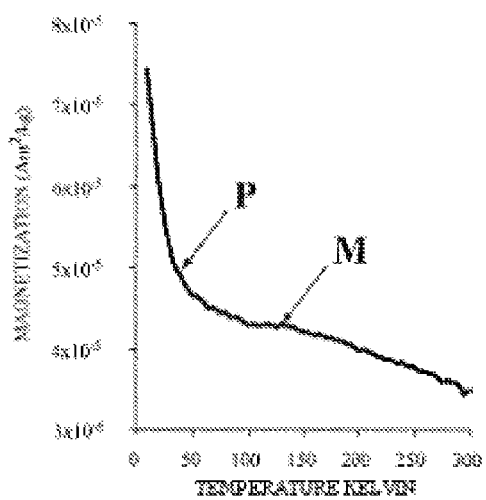

METHOD OF DETERMINING THE MAXIMUM TEMPERATURE UNDERGONE BY A SEDIMENTARY ROCK, ESPECIALLY IN THE FIELD OF HYDROCARBON FORMATION

CROSS REFERENCE TO RELATED APPLICATIONS

This application is a National Stage of International Application No. PCT/FR2009/001391, filed Dec. 4, 2009, which claims priority from French Patent Application No. 0806921, filed Dec. 10, 2008, the contents of all of which are incorporated herein by reference in their entirety.

The present invention relates to a method of determining the maximum temperature undergone by a sedimentary rock during geological heating, for example associated with burying. Of particular interest are sediments that may be the site of hydrocarbon formation or storage. More particularly, this invention relates to methods that characterize magnetic minerals by certain magnetic properties thereof.

It is well known that certain iron compounds, principally oxides and sulfides, show magnetic characteristics enabling them to be identified. The underlying principle on which the present invention is based is that iron sulfides and oxides are modified, or created, by even very moderate heating (approximately 60° C. to 230° C.) and that this results in their magnetic properties being modified.

The temperature range, which covers, from 60° C. to 230° C. approximately, is crucial for providing the conditions for organic matter maturation, and therefore the type of mineral deposit. The transformations involved over the course of thermal impact imply extremely small contents of transformed and/or created minerals, and magnetic methods are perfectly suited for assaying these minerals. By determining the maximum temperature undergone by a number of specimens taken from a formation, it is possible to deduce the maximum temperature undergone by the sampled portion of this formation. In the rest of the description, the method employs a geothermometer intended to determine a paleotemperature.

In the range of paleotemperatures of interest to the oil industry, several techniques are used. The Rock-Eval technique is the one most often used in the oil industry. This technique makes it possible, by heating the specimen (up to 850° C.), to find the characteristics of the organic matter that it contains. The result of this analysis is a temperature $T_{max}$ (400° C. to 700° C.), which is indicative of the degree of maturity of the organic matter. This maximum temperature makes it possible to know where the rock is located in relation to the oil and gas windows. However, the Rock-Eval technique does not give an absolute paleotemperature, $T_{max}$ being a pyrolysis temperature. The paleotemperature is determined by constraining the thermal kinetics of the specimens. Rock-Eval is a destructive method, being applicable only on rock in which the organic matter content exceeds 100 ppm (parts per million). The Rock-Eval technique is applicable in principle only on source rock.

There are optical methods, such as vitrinite reflectance, the degree of alteration of conodonts or acritarches, which make it possible for the degree of maturation of the organic matter to be qualitatively calibrated and to locate said matter in relation to the oil window. Vitrinite reflectance implies the presence of organic matter of ligno-cellulosic origin derived from higher plant matter and therefore absent from marine series often the origin of crude oil. Conodonts and acritarches are fossils that are not encountered in all sedimentary series. Magnetic methods have been described, these being based on studying the remnant magnetizations produced in the sediment by geological heating and cooling. These remagnetizations are combined vectorially with the pre-existing magnetizations, and they remain difficult to isolate.

The object of the invention is therefore to remedy all or some of the aforementioned drawbacks. It aims to provide an evaluation of the maximum temperature reached by a sedimentary formation, rapidly and in a nondestructive manner, on a few milligrams of rock. The invention applies to sedimentary formations of the source rock type that contain organic matter, but also to other formations, for example reservoir rock (carbonates, detrital rock). These sediments will be denoted in the remainder of the text by "the sediments".

It is also known that magnetite ($Fe_3O_4$) appears in the sediments for a heating temperature of about 100° C.

The invention is based on the following discoveries:
1. the discovery of the appearance, in the sediments, of pyrrhotite ($Fe_7S_8$) above a heating temperature as low as 60° C. approximately. This fine-grained pyrrhotite at very low contents will be called in the rest of the description "pyrrhotite P";
2. the discovery of a characteristic magnetic transition of said pyrrhotite P at a temperature close to 35 K. This transition will be called in the rest of the description "transition P"; and
3. the discovery of a specific operating method for demonstrating said low-temperature transition down to a few Kelvin.

The invention describes a method whereby the combination of the magnetic signature of pyrrhotite P with that of magnetite depends on the geological heating temperature of the sediment and constitutes a geothermometer which can be calibrated.

Generally, by analyzing the variation in magnetization of a rock upon cooling it down to a temperature of a few Kelvin, it is possible to detect and identify standard magnetic minerals by the transitions that they undergo.

The two magnetic minerals ($Fe_7S_8$ and $Fe_3O_4$) are in concentrations of the order of 100 parts per million, with grain sizes ranging from the nanoscale to the micron scale. These minerals are therefore not easily detectable by the usual methods of investigation available in the oil industry. The magnetic analysis methods, and in particular low-temperature methods, make it possible to characterize transformed magnetic minerals at concentrations of a few tens of parts per billion.

To analyze these characteristic transitions, it is possible to use for example, but without this being limiting, the variation in isothermal remnant magnetization, called hereafter IRM, preferably at saturation. This IRM can be produced by applying an intense DC magnetic field, for example of 2 tesla or higher. The IRM may be acquired at room temperature and its intensity is monitored as the specimen cools down. The IRM may be produced at low temperature and its intensity is monitored as the specimen warms up. In the examples given, the variation of an IRM acquired at ordinary temperature is monitored during cooling down to 10 K for example and then the variation to room temperature of an IRM acquired at 10 K in the same field is monitored thereafter.

It would also be possible to demonstrate the transitions of the minerals under investigation by monitoring, at the same very low temperatures, the magnetic susceptibility of the sediment, measured either in an AC magnetic field, possibly using several frequencies, or in a DC magnetic field.

More precisely, identification of very fine-grain pyrrhotite P in very small amounts, by its specific transition P, is based on a novel operating method that consists in applying, at least during the cooling step, a low DC magnetic field, for example of the order of 5 microtesla. without applying this low DC field at least during cooling, for example down to 10 K, the transition P may not be detected.

Figure 2:
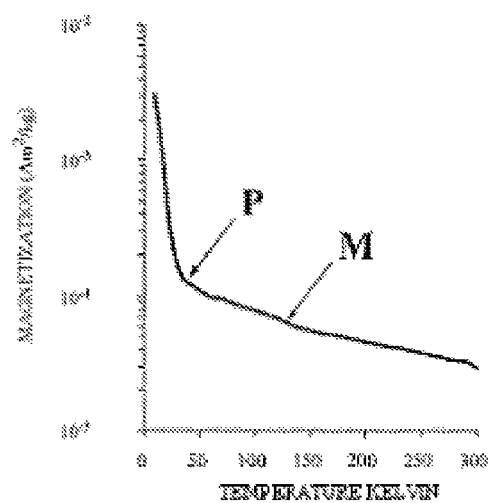
Figure 3:
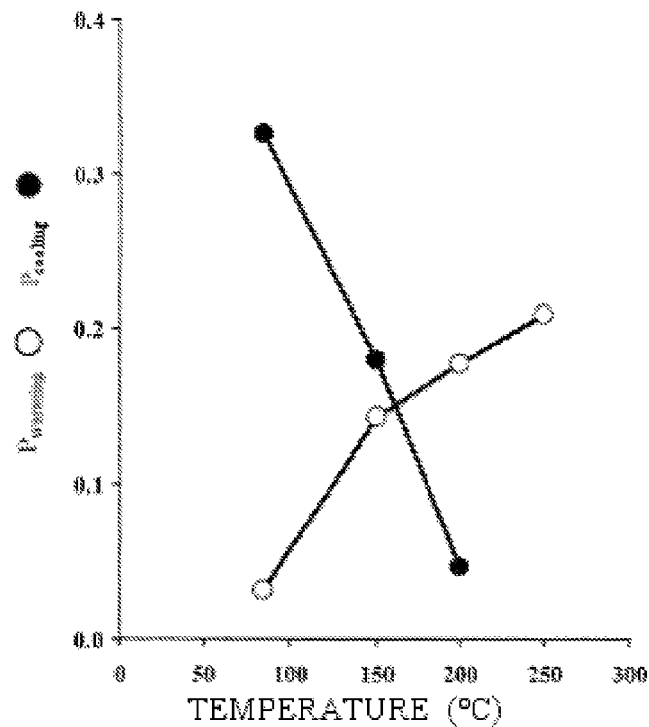

Other features and advantages of the invention will become apparent on examining the following detailed description and the appended drawings given as nonlimiting examples:

FIG. 1 shows the magnetic signature of a specimen of natural Aalenian argillites from the Swiss Jura, indicating the cooling curve for an IRM acquired at a temperature of 300 K;

FIG. 2 shows the magnetic signature of a specimen of natural Aalenian argillites from the Swiss Jura as in FIG. 1, indicating the warming curve for an IRM acquired at the temperature of 10 K; and FIG. 3 shows an example of the calibration of a geothermometer, indicating the variation of two parameters, namely $P_{cooling}$ and $P_{warming}$, derived from curves similar to those presented in FIGS. 1 and 2 respectively.

Referring firstly to FIG. 1, the curve shown represents the variation, upon cooling, in an IRM acquired at ordinary temperature in a magnetic field of 2.5 tesla, called $IRM_{300K}$. The temperatures are plotted on the x-axis and the magnetizations, on the y-axis, are in $Am^2/kg$. The cooling takes place in a low magnetic field of 5 microtesla. The specimen studied was an Aalenian argillite from the Swiss Jura that had undergone a maximum temperature of approximately 85° C. under the effect of being buried over the course of its geological history. A transition at 120 K (called the Verwey transition) indicates the presence of magnetite, denoted by M on the curve. The increase in magnetization above approximately 35 K is characteristic of the transition P, denoted by P on the curve. The transition P may be characterized, for example, by the amplitude of the increase in magnetization between the temperature of 35 K and that of 10 K, i.e. $(IRM_{300K}(10\ K)-IRM_{300K}(35\ K))/IRM_{300K}(10\ K)$ in which the first temperature, subscripted, indicates the IRM acquisition temperature and the second, in brackets, indicates the measurement temperature.

In FIG. 2, the curve shows the variation upon warming from 10 K to 300 K for an IRM acquired in the same 2.5 T field at the temperature of 10 K, called $IRM_{10K}$. The specimen is the same as that of FIG. 1. The temperature in Kelvin is plotted on the x-axis and the magnetization, in $Am^2/kg$, is plotted on the y-axis on a logarithmic scale. The Verwey transition, denoted by M on the curve, indicates the presence of magnetite at 120 K. The reduction in magnetization from 10 K to 35 K is another characteristic of the transition P, denoted by P on the curve. The transition P may therefore also be characterized, for example, by the amplitude of the reduction in magnetization between a temperature of 10 K and that of 35 K, i.e. $IRM_{10K}(35\ K)/IRM_{10K}(10\ K)$ in which the first temperature, subscripted, indicates the IRM acquisition temperature and the second, in brackets, indicates the measurement temperature.

It should be noted that the variations in magnetization shown in FIG. 1 and FIG. 2 are, for each temperature, mainly the result of the combination of the magnetization of the pyrrohotite and that of the magnetite, without it being possible to exclude lesser contributions from other minerals.

Two parameters are thus defined that may serve to characterize the magnetic transitions appearing in the experiment described in FIG. 1. These parameters are given as nonlimiting examples, and other parameters characteristic of the transitions or concentrations of pyrrohotite and magnetite could also be used:

from the $IRM_{300K}$ cooling curve of FIG. 1:

$$P_{cooling}=(IRM_{300K}(10\ K)-IRM_{300K}(35\ K))/IRM_{300K}(10\ K);\ and$$

from the $IRM_{10K}$ warming curve in FIG. 2:

$$P_{warming}=IRM_{10K}(35\ K)/IRM_{10K}(10\ K).$$

Referring now to FIG. 3, this shows a calibration of the geothermometer based on the variations in the parameters $P_{cooling}$ and $P_{warming}$ as a function of the laboratory heating temperatures determined on the same sediment. The heating is carried out in sealed gold capsules. The heating temperatures, namely 150° C., 200° C. and 250° C., are plotted on the x-axis and the measured ratios, $P_{warming}$ and $P_{cooling}$, are plotted on the y-axis. Also given are the parameters measured on the specimen of the natural sediment heated over the course of its geological history, as shown in FIGS. 1 and 2. The values of $P_{cooling}$ and $P_{warming}$ are indicated in the table below. It should be noted that there is no $P_{warming}$ value at 250° C. as the transition P was not detected in the cooling curve for the $IRM_{300K}$. The invention proposes that the $P_{warming}$ and $P_{cooling}$ ratios, or any other ratio derived from other parameters giving a good estimation of the contributions of magnetite and pyrrohotite, provide an estimate of the maximum temperature undergone by the sediment in order to serve as a geothermometer in the temperature range from 60° C. to 230° C. approximately. The $P_{warming}$ and $P_{cooling}$ ratios, as indicated in the table, may serve as an example of how to calibrate the geothermometer. The temperature reached by the rock in the natural state is taken from the literature, and is given to within 20%. The laboratory temperatures are precise to within 1°.

TABLE

| Argillite specimen | Natural | Lab. | Lab. | Lab. |
|---|---|---|---|---|
| Temperature | 85° C. | 150° C. | 200° C. | 250° C. |
| $P_{warming}$ | 0.03 | 0.14 | 0.18 | 0.21 |
| $P_{cooling}$ | 0.33 | 0.18 | 0.05 | — |

These calibration values give the maximum temperature, or paleotemperature, undergone by a specimen of the geological formation investigated, more generally by a specimen of argillites, for comparison with the $P_{warming}$ and $P_{cooling}$ ratios provided by the measurement carried out on this specimen according to the illustrative example of the method described above. It is therefore estimated that this paleotemperature is given to within approximately 15° C. It is not excluded that corrections would have to be made to these calibration values for different rock families, such as many limestone or silty rock, for example. These corrections may be determined by laboratory heating or by any other method that could give temperature indicators.

If greater precision is necessary, for example when it is desired to monitor the variation in paleotemperature of specimens removed from a drill hole, a specific calibration is described below. After the factors $P_{warming}$ and $P_{cooling}$ of a specimen have been measured and the paleotemperature thereof determined, it is possible to heat said specimen again, in the laboratory, to temperatures slightly below and/or slightly above the paleotemperature found, for example 10° C. higher. A new measurement according to the method is carried out. The $P_{warming}$ and $P_{cooling}$ ratios lead to a new found temperature that should be equal to the temperature to which the specimen was heated in the laboratory, if said temperature is above the paleotemperature. On the other hand, if the warming temperature found remains equal to the paleotemperature, it may be deduced therefrom that this paleotemperature is slightly underestimated. The paleotemperature measurement may or may not be further refined. This heating may advantageously take place in an appropriate compartment, in the same place as the measurement of the magnetic transitions at very low temperature down to a few Kelvin for example, without moving the specimen from the nonmagnetic specimen door, adapted to the use temperatures.

The invention is not limited to the illustrative example of the method described above solely by way of example but rather it encompasses all variants that a person skilled in the art might envisage within the scope of the following claims.

The invention claimed is:

1. A method of determining the maximum temperature undergone by a specimen of sedimentary rock during natural heating over a geological process, within the range from 60° C. to 230° C. approximately, comprising the following steps:
   a. analysis at very low temperature, down to a few kelvin of the magnetic transitions intended to characterize an iron oxide and an iron sulfide that are formed or destroyed in the specimen by the geological heating of the sediment; and
   b. determination of the maximum temperature undergone by the specimen, using a calibration obtained by measuring the same magnetic parameters on the same sediment or on other sediments of the same nature, heated beforehand in the laboratory to known temperatures.

2. The method as claimed in claim 1, characterized in that the iron oxide is magnetite and the iron sulfide is pyrrhotite.

3. The method as claimed in claim 1, characterized in that the measured transitions are magnetic transitions characteristic of magnetite and pyrrhotite and which occur at fixed temperatures lying between approximately room temperature and a few kelvin.

4. The method as claimed in claim 1, characterized in that the magnetic transitions are detected by monitoring the variation in an artificial isothermal remnant magnetization produced by a high DC magnetic field for at least the magnetite and the pyrrhotite to be magnetically saturated.

5. The method as claimed in claim 1, characterized in that a low-intensity DC magnetic field is applied at least during the cooling down to a few Kelvin.

6. The method as claimed in claim 1, characterized in that the magnetic transitions are also detected by monitoring the variation in the magnetic susceptibility of the specimen at low temperatures, down to a few degrees K.

7. The method as claimed in claim 1, wherein the analysis at very low temperature is down to 10 Kelvin.

8. The method as claimed in claim 1, characterized in that the measured transitions are magnetic transitions characteristic of magnetite and pyrrhotite and which occur at fixed temperatures lying between approximately room temperature and down to 10 K.

9. The method as claimed in claim 1, characterized in that the role of the applied low-intensity DC magnetic field, at least during the cooling down to a few kelvin, is to detect a new transition of the pyrrhotite, called transition P.

10. The method as claimed in claim 9, wherein the cooling down is down to 10 K.

11. The method as claimed in claim 1, characterized in that a low-intensity DC magnetic field of the order of 5 microtesla is applied at least during the cooling down to a few Kelvin.

12. The method as claimed in claim 11, wherein the cooling down is down to 10 K.

* * * * *